US011181501B2

(12) United States Patent
Vellaisamy et al.

(10) Patent No.: US 11,181,501 B2
(45) Date of Patent: Nov. 23, 2021

(54) METHOD AND AN APPARATUS FOR DETERMINING A PRESENCE OR AN AMOUNT OF A POLYAMINE OR ITS DERIVATIVE IN A SAMPLE

(71) Applicant: City University of Hong Kong, Kowloon (HK)

(72) Inventors: A. L. Roy Vellaisamy, Kowloon (HK); Chi-Chung Yeung, Sheung Shui (HK); Shishir Venkatesh, Shatin (HK); Hon-Wah Lam, Kowloon (HK)

(73) Assignee: City University of Hong Kong, Kowloon (HK)

( * ) Notice: Subject to any disclaimer, the term of this patent is extended or adjusted under 35 U.S.C. 154(b) by 63 days.

(21) Appl. No.: 16/127,321

(22) Filed: Sep. 11, 2018

(65) Prior Publication Data

US 2020/0080960 A1    Mar. 12, 2020

(51) Int. Cl.
*G01N 27/414* (2006.01)
*G01N 27/22* (2006.01)
(Continued)

(52) U.S. Cl.
CPC ....... *G01N 27/4145* (2013.01); *G01N 27/221* (2013.01); *G01N 27/226* (2013.01);
(Continued)

(58) Field of Classification Search
CPC ............. G01N 27/4145; G01N 27/221; G01N 27/226; G01N 33/493; G01N 2800/342; C08G 73/02
See application file for complete search history.

(56) References Cited

U.S. PATENT DOCUMENTS

| 5,126,247 A | 6/1992 | Palmer et al. |
| 2012/0222958 A1 | 9/2012 | Pourmand et al. |

(Continued)

FOREIGN PATENT DOCUMENTS

| CN | 105907844 | 8/2016 |
| WO | 2013022545 | 2/2013 |

(Continued)

OTHER PUBLICATIONS

Minami, Tsuyoshi, et al. "An extended-gate type organic FET based biosensor for detecting biogenic amines in aqueous solution." Analytical Sciences 31.7 (2015): 721-724. (Year: 2015).*

(Continued)

*Primary Examiner* — Robert J Eom
(74) *Attorney, Agent, or Firm* — Renner Kenner Greive Bobak Taylor & Weber (57) ABSTRACT

A method and an apparatus for determining a presence or an amount of a polyamine or its derivative in a sample, the method including: applying the sample on an electrochemical detector having a substance selection structure, wherein the substance selection structure is sensitive to the polyamine or its derivative; applying at least one voltage bias to the electrochemical detector; and detecting a change of electrical characteristics of the electrochemical detector so as to determine the presence or the amount of the polyamine or its derivative in the sample.

18 Claims, 6 Drawing Sheets

(51) Int. Cl.
*G01N 33/493* (2006.01)
*C08G 73/02* (2006.01)

(52) U.S. Cl.
CPC ........... *G01N 33/493* (2013.01); *C08G 73/02* (2013.01); *G01N 2800/342* (2013.01)

(56) References Cited

U.S. PATENT DOCUMENTS

| | | |
|---|---|---|
| 2015/0232913 A1 | 8/2015 | Reardon |
| 2018/0149632 A1 | 5/2018 | Vellaisamy et al. |

FOREIGN PATENT DOCUMENTS

| | | |
|---|---|---|
| WO | 2013185078 | 12/2013 |
| WO | 2017165800 | 9/2017 |
| WO | 2018106625 | 6/2018 |

OTHER PUBLICATIONS

Trikka, Foteini A., et al. "Molecularly imprinted polymers for histamine recognition in aqueous environment." Amino Acids 43.5 (2012): 2113-2124. (Year: 2012).*

Yang, Haoyue, Shoichi Nishitani, and Toshiya Sakata. "Potentiometric Langmuir Isotherm Analysis of Histamine-Selective Molecularly Imprinted Polymer-Based Field-Effect Transistor." ECS Journal of Solid State Science and Technology 7.7 (2018): Q3079. (Year: 2018).*

\* cited by examiner

METHOD AND AN APPARATUS FOR DETERMINING A PRESENCE OR AN AMOUNT OF A POLYAMINE OR ITS DERIVATIVE IN A SAMPLE

TECHNICAL FIELD

The present invention relates to a method and an apparatus for determining a presence or an amount of a polyamine or its derivatives in a sample in particular a biological sample, specifically, although not exclusively, to a method and an apparatus for detecting biomarkers in a biological sample.

BACKGROUND

A disease is any condition that impairs the normal functioning of the body, which can be generally divided into infectious and non-infectious. Importantly, any improper or delay treatment of a disease could lead to a fatal consequence to a patient, regardless of what type of the disease is. Thus, the screening and diagnosis of the disease is of paramount importance.

Traditional screening methods usually include invasive procedures during sampling process. The screening methods are also time-consuming and require tedious instruments installed in laboratories for carrying out the measurements. Although the results generated therefrom may be very accurate and sensitive, such methods may not be suitable for daily applications which require point-of-care and low-cost setup.

SUMMARY OF THE INVENTION

In accordance with the first aspect of the present invention, there is provided a method of determining a presence or an amount of a polyamine or its derivative in a sample, comprising the steps of: applying the sample on an electrochemical detector having a substance selection structure, wherein the substance selection structure is sensitive to the polyamine or its derivative; applying at least one voltage bias to the electrochemical detector; and detecting a change of electrical characteristics of the electrochemical detector so as to determine the presence or the amount of the polyamine or its derivative in the sample.

In an embodiment of the first aspect, the polyamine includes urinary spermine.

In an embodiment of the first aspect, the sample includes a biological sample.

In an embodiment of the first aspect, the substance selection structure includes a molecule-selective electrode.

In an embodiment of the first aspect, the molecule-selective electrode comprises a polymer layer arranged to bind with the polyamine or its derivative, and wherein the sample is in contact with the polymer layer.

In an embodiment of the first aspect, the polymer layer includes a molecular imprinted polymer.

In an embodiment of the first aspect, the molecular imprinted polymer is selective to a predetermined polyamine or its derivative.

In an embodiment of the first aspect, the electrochemical detector further comprises an electronic device in electrical communication with the substance selection structure.

In an embodiment of the first aspect, the change of electrical characteristics of the electrochemical detector is induced by a change in a differential capacitance of the substance selection structure.

In an embodiment of the first aspect, the change of electrical characteristics of the electrochemical detector is induced by a change in a permittivity and/or a dielectric constant of the polymer layer binding with a different amount of polyamine or its derivative.

In an embodiment of the first aspect, the electronic device includes a transistor.

In an embodiment of the first aspect, the substance selection structure is in electrical communication with a gate electrode of the transistor.

In an embodiment of the first aspect, the substance selection structure is arranged to operate as a gate electrode of the transistor.

In an embodiment of the first aspect, the electrical characteristic includes a threshold voltage of the transistor.

In an embodiment of the first aspect, the electrical characteristic includes a saturation drain current across the transistor under a predetermined gate bias and a predetermined source-drain bias.

In an embodiment of the first aspect, the gate bias is applied across the sample applied on the substance selection structure, the substance selection structure and the transistor.

In accordance with the second aspect of the invention, there is provided a method of diagnosing prostate cancer in a subject, comprising the steps of determining a concentration of urinary spermine in a sample associated with the subject, wherein the concentration of urinary spermine is determined by the method of determining a presence or an amount of a polyamine or its derivative in a sample in accordance with the first aspect.

In accordance to the third aspect of the invention, there is provided an apparatus for determining a presence or an amount of a polyamine or its derivative in a sample, comprising: a substance selective structure configured to interact with the polyamine or its derivative present in the sample; and an electronic device in electrical connection with the substance selective structure; wherein the substance selective structure is arranged to alter an electrical characteristic of the electronic device upon a chemical interaction between the substance selective structure with the polyamine or its derivative, thereby indicating the presence or the amount of the polyamine or its derivative in the sample based on the electrical characteristic altered by the chemical interaction.

In an embodiment of the third aspect, the polyamine includes urinary spermine.

In an embodiment of the third aspect, the sample includes a biological sample.

In an embodiment of the third aspect, the substance selection structure includes a molecule-selective electrode.

In an embodiment of the third aspect, the molecule-selective electrode comprises a polymer layer arranged to bind with the polyamine or its derivative, and wherein the sample is in contact with the polymer layer.

In an embodiment of the third aspect, the polymer layer includes a molecular imprinted polymer.

In an embodiment of the third aspect, the molecular imprinted polymer is selective to a predetermined polyamine or its derivative.

In an embodiment of the third aspect, the change of electrical characteristics of the electronic device is induced by a change in a differential capacitance of the substance selection structure.

In an embodiment of the third aspect, the change of electrical characteristics of the electronic device is induced by a change in a permittivity and/or a dielectric constant of the polymer layer binding with a different amount of polyamine or its derivative.

In an embodiment of the third aspect, the electronic device includes a transistor.

In an embodiment of the third aspect, the substance selection structure is in electrical communication with a gate electrode of the transistor.

In an embodiment of the third aspect, the substance selection structure is arranged to operate as a gate electrode of the transistor.

In an embodiment of the third aspect, the electrical characteristic includes a threshold voltage of the transistor.

In an embodiment of the third aspect, the electrical characteristic includes a saturation drain current across the transistor under a predetermined gate bias and a predetermined source-drain bias.

In an embodiment of the third aspect, the gate bias is applied across the sample on applied on the substance selection structure, the substance selection structure and the transistor.

BRIEF DESCRIPTION OF THE DRAWINGS

Embodiments of the present invention will now be described, by way of example, with reference to the accompanying drawings in which.

DETAILED DESCRIPTION OF THE PREFERRED EMBODIMENT

Cancer is one of the mortal diseases in the world. In particular, prostate cancer is one of the most common types of cancer. Recent studies have shown that around 1 million men are diagnosed with prostate cancer each year, with a mortality rate of about 17%. However, the 5-year survival rate is 100% if the cancer is diagnosed in the local stage. Thus, diagnostic tools enabling the screening test of cancer become of paramount importance.

The inventors have, through their own research, trails and experiments, devised that several methods may be used for prostate cancer screening. For example, prostate-specific antigen (PSA) test and biopsy test are two of the tests commonly used in the art. However, these tests either require invasive sample collection or time-consuming analysis, whilst both of which further require a trained person to operate.

Figure 1:
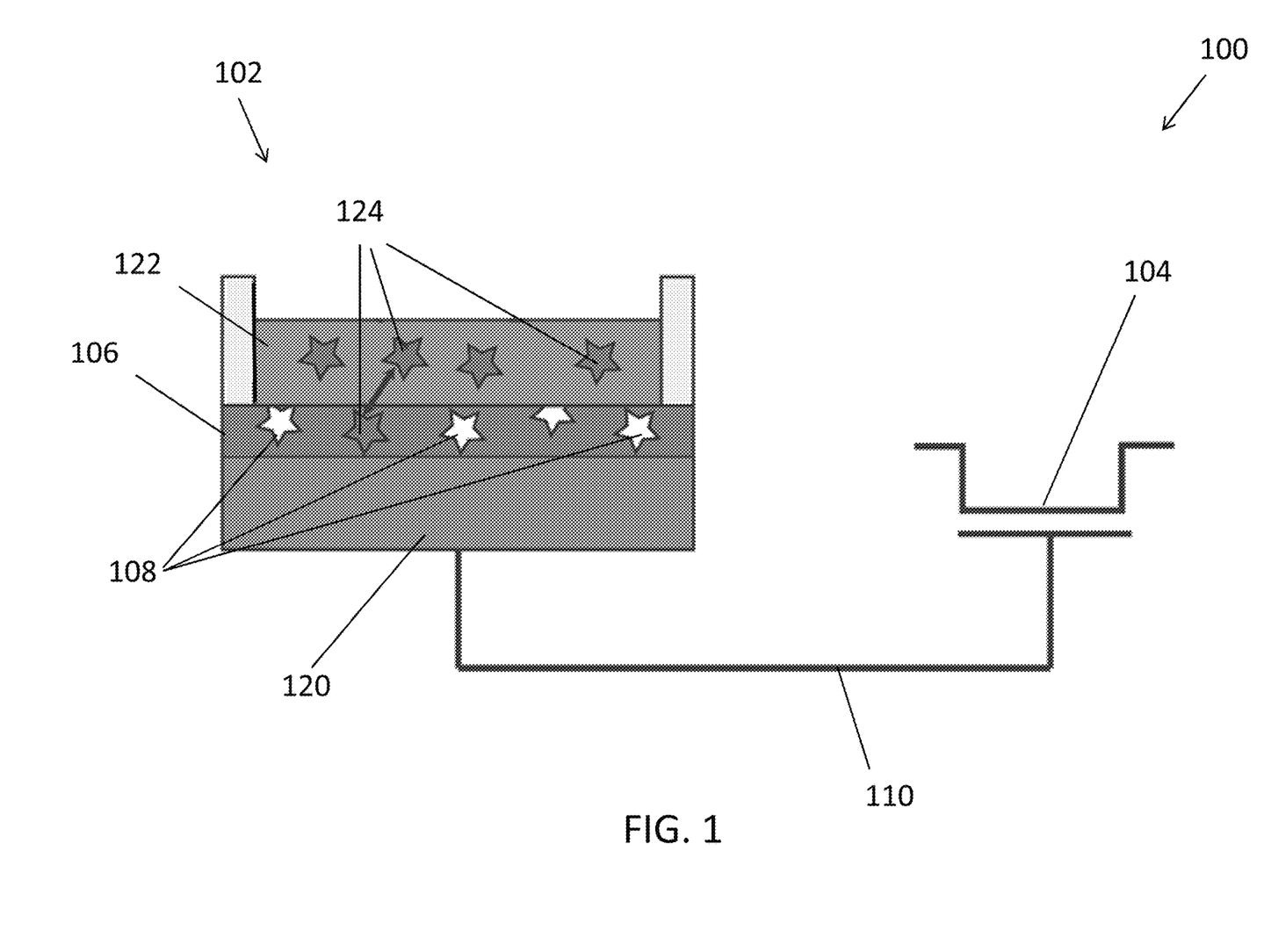
FIG. 1 is a schematic diagram showing an apparatus for determining a presence or an amount of a polyamine or its derivative in a sample, and an interaction between a polyamine molecule and the substance selection structure in accordance with one embodiment of the present invention.

With reference to FIG. 1, there is shown an embodiment of an apparatus for determining a presence or an amount of a polyamine 124 or its derivative in a sample 122, comprising: a substance selective structure 102 configured to interact with the polyamine 124 or its derivative present in the sample 122; and an electronic device 104 in electrical connection with the substance selective structure 102; wherein the substance selective structure 102 is arranged to alter an electrical characteristic of the electronic device 104 upon a chemical interaction between the substance selective structure 102 with the polyamine 124 or its derivative, thereby indicating the presence or the amount of the polyamine 124 or its derivative in the sample 122 based on the electrical characteristic altered by the chemical interaction.

In this embodiment, the apparatus 100 may be used as an electrochemical detector for detecting polyamine or its derivative in a sample. The apparatus 100 includes a substance selective structure 102 which may selectively interact with one or more target substance 124. By determining the amount of target substance 124 interacting with the substance selective structure 102, the concentration of the target substance 124 in a testing sample 122 may be further determined.

For example, substance selection structure 102 which includes chemical receptors arranged to interact with other chemical substances which are in contact with the substance selection structure 102. Preferably, the substance selection structure 102 may include a molecule-selective electrode, and the substance selection structure may interact with at least one molecule of the target substance 124.

The molecule-selective electrode 102 may be specifically designed for facilitating the detection of polyamine molecules in the analyte solution. Alternatively, the molecule-selective electrode 102 may include different structures and/or components for the detection of different/multiple target substances.

Referring to FIG. 1, the molecule-selective electrode 102 comprises a polymer layer 106. Preferably, the polymer layer may be a molecular imprinted polymer (MIP), in which the polymer layer 106 is provided with a plurality of voids 108 each arranged to accommodate a molecule of the target substance, therefore the polymer layer 106 may accommodate the molecules of the target substance 124 when the target substance is in contact with the polymer layer 106.

In this example, each of the plurality of voids 108 includes a structure (such as a molecular structure) matching with a molecular structure of the polyamine or its derivative in a testing sample 122 in contact with the molecule-selective electrode 102. The voids 108 are selective to polyamine or its derivative and may accommodate only the matching molecules of the target substance 124. The polymer layer 106 will not interact with substance with any molecular structures which do not match with the molecular imprinted structure.

Preferably, the molecular imprinted polymer 106 may include voids 108 which are selective to biomarkers in a biological sample. A presence or a concentration of certain biomarkers in a sample may indicate a possibility of suffering from a known disease, such as cancer.

When the target substance 124 (such as polyamine or its derivatives) in the sample 122 is in contact with the MIP layer 106, the voids 108 accommodate one or more molecules of the target substance 124. Upon the interaction between the polyamine or its derivatives and the substance selection structure 102, the permittivity and hence the dielectric constant and the electrical capacitance of the molecular imprinted polymer layer 106 is changed.

The chemical interaction may be transformed to or represented as an electrical signal which may be further captured or detected using electrical characterization methods. For example, With reference to FIG. 1, the apparatus 100 further comprises an electronic device 104 in electrical connection with the substance selective structure 102. Accordingly, by determining the changes in electrical characteristic of the electronic device 104 induced by the chemical interactions occur in the substance selection structure 102, the presence or the amount of the polyamine or its derivative in the sample 122 may be determined.

In one example embodiment, the electronic device 104 is a field effect transistor (FET) such as a thin-film transistor (TFT) or a metal-oxide semiconductor FET (MOSFET). An electronic transistor may be characterized by different electrical characteristics such as threshold voltage (or turn on voltage) and source-drain current under different predetermined (gate and source-drain) voltage bias conditions.

Preferably, the substance selection structure 102 may be electrically connected to the gate terminal the FET 104, the substance selection structure 102 may operate as a gate electrode of the FET 104. In such configuration, the gate voltage signal may be applied to the FET 104 via the molecular imprinted polymer 106.

In an example operation of the apparatus 100, a fix positive or negative gate bias may be applied using an electric source as the gate voltage bias, and the threshold voltage of the FET 104 may be changed due to an interaction between the target substance 124 and the molecular imprinted polymer 106, therefore the source-drain current across the source and drain electrodes may be increased/decreased when compare to the drain current under a same external gate/source/drain voltage bias applied to the transistor without a target substance in contact with the molecular imprinted polymer layer 106, due to a change of gate capacitance of the extended gate structure 102. A change in a permittivity and/or a dielectric constant of the polymer layer binding with a different amount of polyamine or its derivative effectively changes the gate capacitance of the extended gate structure 102.

Figure 2:
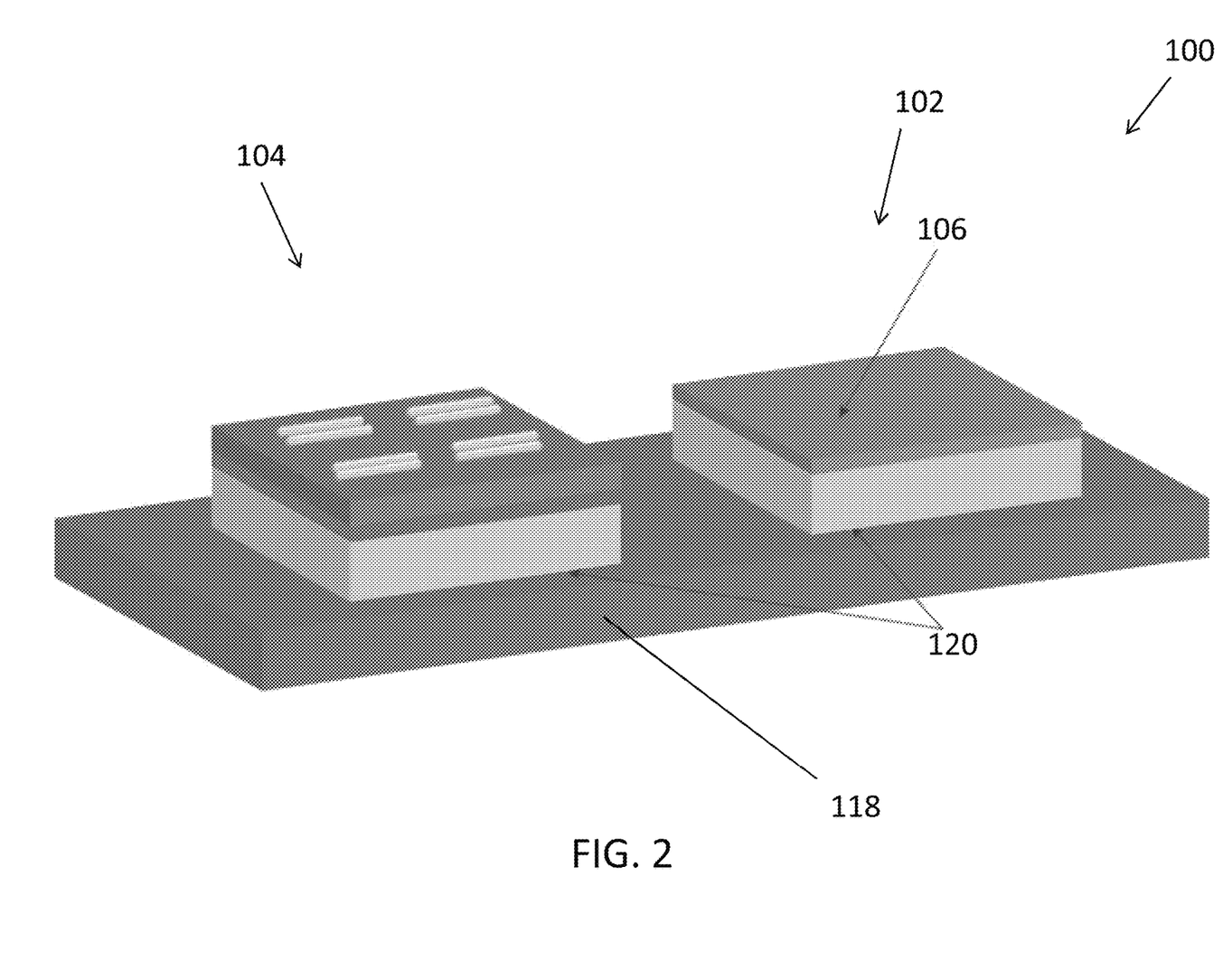
FIG. 2 is a perspective view of an apparatus for determining a presence or an amount of a polyamine or its derivative in a sample in accordance with one embodiment of the present invention.

With reference to FIG. 2, there is shown an electrochemical detector 100 in accordance with an alternative embodiment of the present invention. In this embodiment, the electronic device 104 and the substance selection structure 102 are electrically and physically connected by an intermediate substrate 118, such that electrical signal may be transmitted between different individual structures.

For example, the intermediate substrate 118 may include a copper substrate, or it may include an electrically conductive substrate, such as but not limited to an aluminum foil and a glass substrate coated with indium-doped tin oxide (ITO). The intermediate substrate 118 may also provide mechanical support to different structures disposed thereon.

In some example embodiments, the substance selection structure 102 and electronic device 104 may be individual devices, which may be electrically connected by electrical wires or any electrical connection means 110 as appreciated by a skilled person. Alternatively, the substance selection structure 102 and electronic device 104 may be mounted on a non-conductive substrate and are electrically connected through an external electrical connection 110.

Figure 3A:
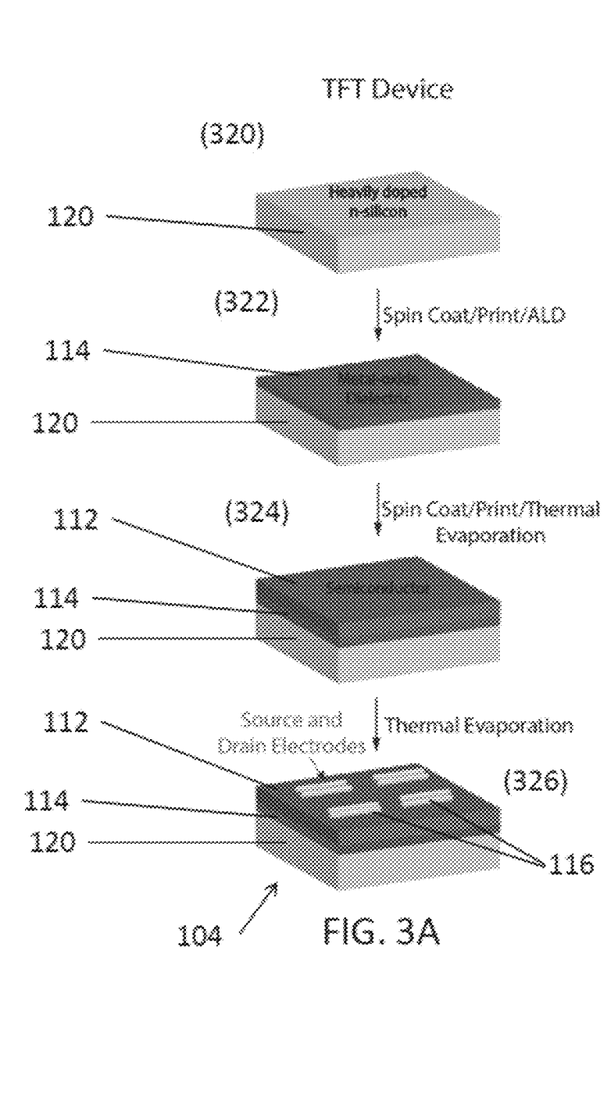
FIG. 3A is an illustration showing a process flow of fabrication of an electronic device structure of the apparatus for determining polyamine of FIG. 2.
Figure 3B:
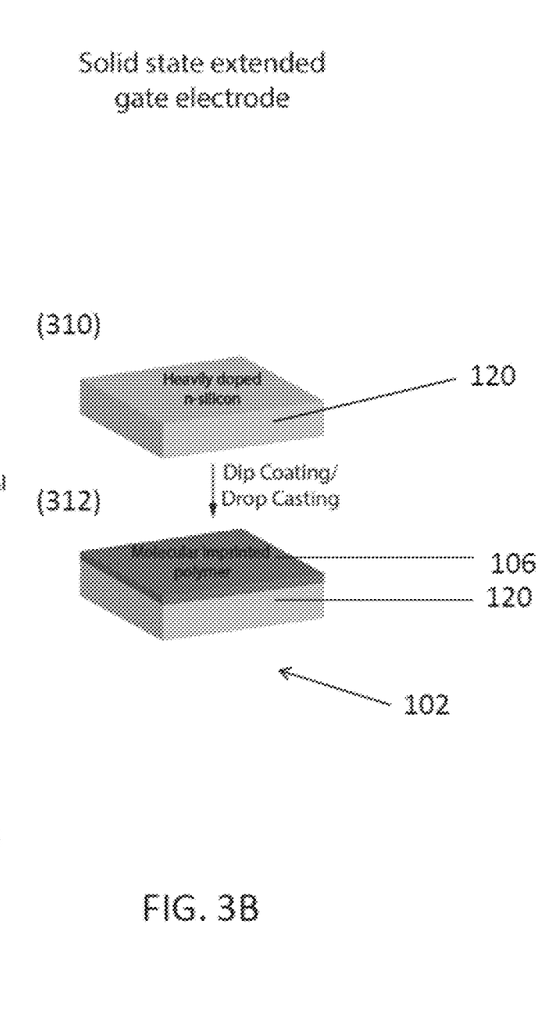
FIG. 3B is an illustration showing a process flow of fabrication of a substance selection structure of the apparatus for determining polyamine of FIG. 2.
Figure 3C:
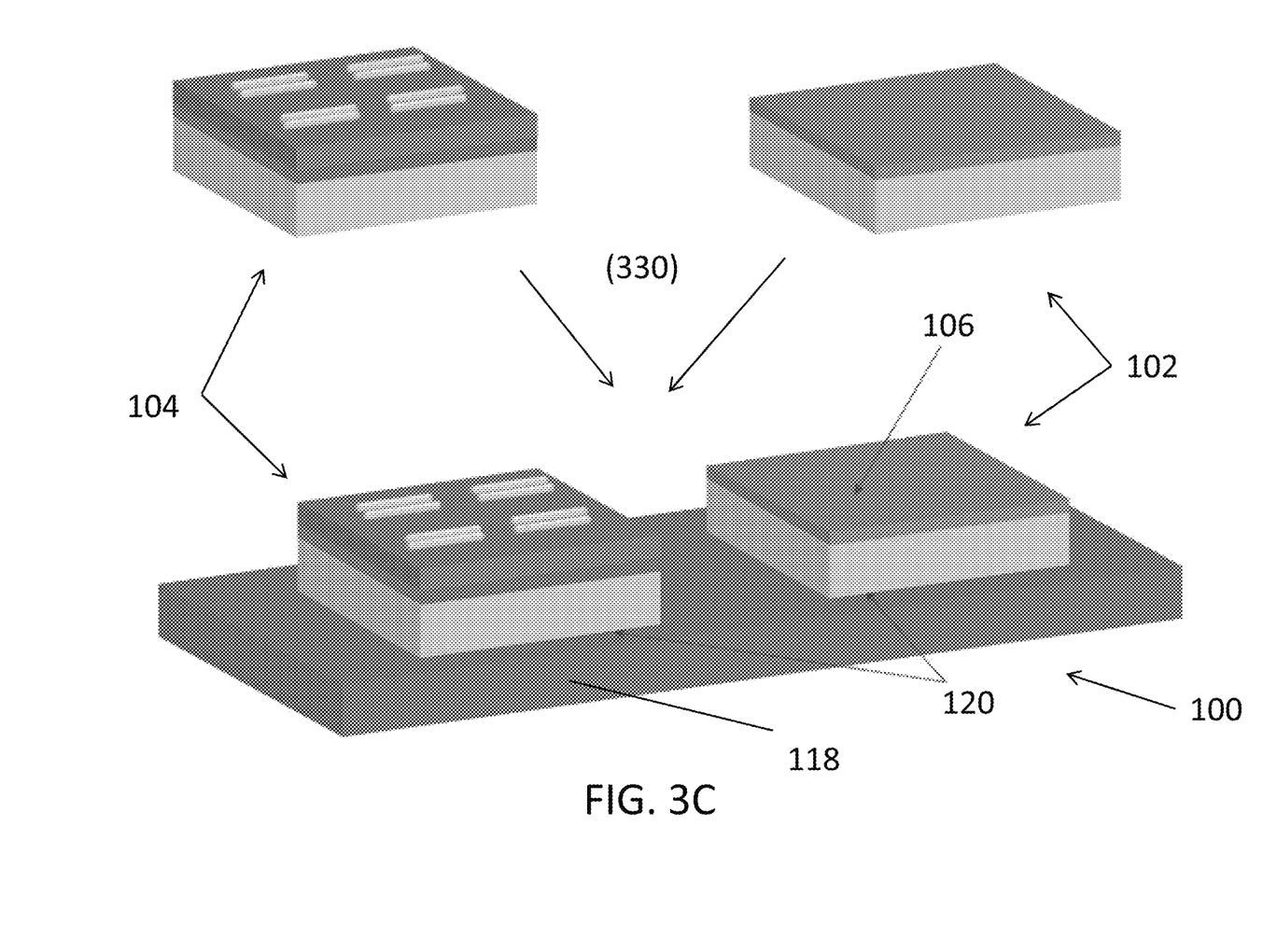
FIG. 3C is an illustration showing the combination of the electronic device structure of FIG. 3A and the substance selection structure of FIG. 3B in the fabrication of the apparatus for determining polyamine of FIG. 2.

With reference to FIGS. 3A to 3C, there is shown an example embodiment of a fabrication of the apparatus 100. In this embodiment, a substance selection structure 102 and an electronic device structure 104 are fabricated on a plurality of separate substrates 120 (such as heavily doped semiconductor substrates or metal substrates), and the two fabricated structures may be further electrically connected to an intermediate copper substrate 118.

To fabricate the substance selection structure 102, at step 310, a heavily n-doped (n+) silicon substrate 120 is cleaned with standard cleaning procedures. At step 312, the molecular imprinted polymer 106 is deposited on the surface of the silicon substrate 120.

The MIP layer 106 may be prepared using electro-polymerization method, by firstly mixing polyamines (e.g. spermine) with a conjugated molecule (e.g. phenol, aniline, pyrrole, etc.) with an acid functional group (carboxylic or sulfonic group) in a pH buffer solution (e.g. PBS) at neutral or acidic pH. After the solution is well mixed, the solution may be transferred onto a conducting surface (e.g. ITO coated glass) to carry out a cyclic voltammetry process (10 cycles) to initiate an electro-polymerization process. After completing half of the process (5 cycles), a negative potential may be applied to the conducting surface for 1 minute to ensure the binding of polyamine to the as-formed polymer.

Under a neutral or an acidic pH condition, the amine groups of the polyamines generally have a positive charge and basic properties. As such, by reacting with a monomer with an acid functional group, a strong binding between the monomer and the polyamine may be achieved.

After the electro-polymerization process is completed, the silicon substrate 120 may be immersed in the buffer solution containing the electro-polymer for 24 hours to facilitate the extraction of the polyamine template from the polymer layer. The polyamines may be extracted and removed from the deposited polymer layer by applying a positive potential to the polymer for 2 minutes. Finally, the substrate with a MIP layer thereon may then be rinsed with fresh buffer solution, and dried under nitrogen.

In an alternative embodiment, the MIP layer 106 may be prepared by mixing a monomer, a cross-linker, a radical initiator and a template of the target substance. After the solution was well mixed, the solution may be degassed by nitrogen, then a polymerization catalyst may be added to initiate the fabrication. The solution may be kept for 16 hours in order to complete the polymerization. By completing such polymerization process, a combination of a molecular-imprinted polymer and a molecular template of the target substance is fabricated.

The fabricated combined MIP and template may be filtered, washed and dried under nitrogen atmosphere, and may then be ground and sieved to obtain a plurality of polymer particles each having a size of around 50 µm. The molecular template may then be extracted and removed from the MIP by the Soxhelt extraction in 24 hour with methanol. Finally, the MIP powder may be dried under a nitrogen atmosphere.

The MIP may be mixed with trichlorosilane and dropped cast on the surface of the silicon substrate 120. Alternatively, any other solvent suitable for dissolving the MIP polymer particles may be used. The solvent may then be driven away in a following drying process (e.g. under a nitrogen atmosphere) so as to form the MIP layer 106.

Alternatively, the prepared MIP may be deposited on the clean silicon substrate 120 by any solution process such as spin coating, sol-gel, printing, spray coating and/or screen printing.

The thickness of the MIP layer 106 is preferably at approximately 50-100 μm. The performance of the electrochemical apparatus 100 may depend on the MIP particle size, in which the response time of the electrochemical detector may be reduced by reducing the particle size. In addition, the response time may also be reduced by reducing the thickness of the MIP layer 106 on the substance selection structure 102, without affecting the detection limit and/or the linear dynamic range of the electrochemical apparatus 100.

To fabricate the FET structure 104, at step 320, an n+ silicon substrate 120 is cleaned with standard cleaning procedures. At step 322, the metal-oxide dielectric (e.g. $HfO_2$, $Al_2O_3$) layer 114 is coated on top of the silicon substrate 120 using either solution process sol-gel method (spin coating, printing. etc.) or atomic layer deposition (ALD), and preferably the dielectric layer has a thickness of 5 nm-10 nm. Preferably, such dielectric layer may operate as a gate dielectric of the FET device 104.

At step 324, a semiconductor layer (n-type semiconductor) 112 is deposited using thermal evaporation or formed through a solution process sol-gel method (spin coating, printing. etc.) or any other suitable fabrication methods as discussed earlier. In this process, 30 nm-50 nm of semiconductor layer 112 is formed on top of the gate dielectric layer, which may operate as the active layer of the FET device 104.

At step 326, gold or other suitable metal pads 116 are deposited on the semiconductor layer 112 which form the source and drain electrodes of the FET device 104. The metal pads 116 may be deposited with thermal evaporation through a shadow-mask with the desired patterns. Alternatively, a conformal layer of metal may be patterned using conventional photolithography methods and other suitable deposition methods to form the metal pads 116. Preferably, the metal pads may include a thickness of 30 nm-50 nm.

The abovementioned ranges of thickness of different layers may be changed in according to requirements or applications of the electrochemical detector.

The fabricated substance selection structure 102 and FET structure 104 may be connected to the intermediate copper substrate 118 at step 330. For example, conductive adhesive may be applied to connect the two structures, either on the same side or opposite sides, to the copper substrate 118. In such configuration, the substance selection structure 102 may operate as an extended gate electrode of the FET device 104. Alternatively, the substance selection structure 102 and the FET structure 104 may be connected without an intermediate substrate 118, or the two different structures may be fabricated on the same substrate such as on a same side of a silicon substrate 120 or on opposite sides on a double-side polished silicon substrate 120, in which the electrical signal between the two structures may be transmitted through the silicon substrate 120.

In an alternative example, the two structures may be fabricated as separate devices and may be further connected using an external electrical connection between the extended gate structure and the gate electrode of the transistor.

In yet another example embodiment, the MIP layer 106 may be fabricated with two or more molecule templates such that the detector may detect the corresponding two or more target analytes. Alternatively, multiple substance selection structures 102 each includes an MIP layer 106 prepared with different molecular templates may be connected to the intermediate copper substrate 118, such that the apparatus 100 may detect different target analytes applied to each of the different substance selection structures 102. It is particularly advantageous when a disease or a cancer is characterized by more than one biomarker. With the multiple substance selection structures configuration, the levels of more than one biomarker may be determined at the same time to provide efficient screening process.

Figure 4:
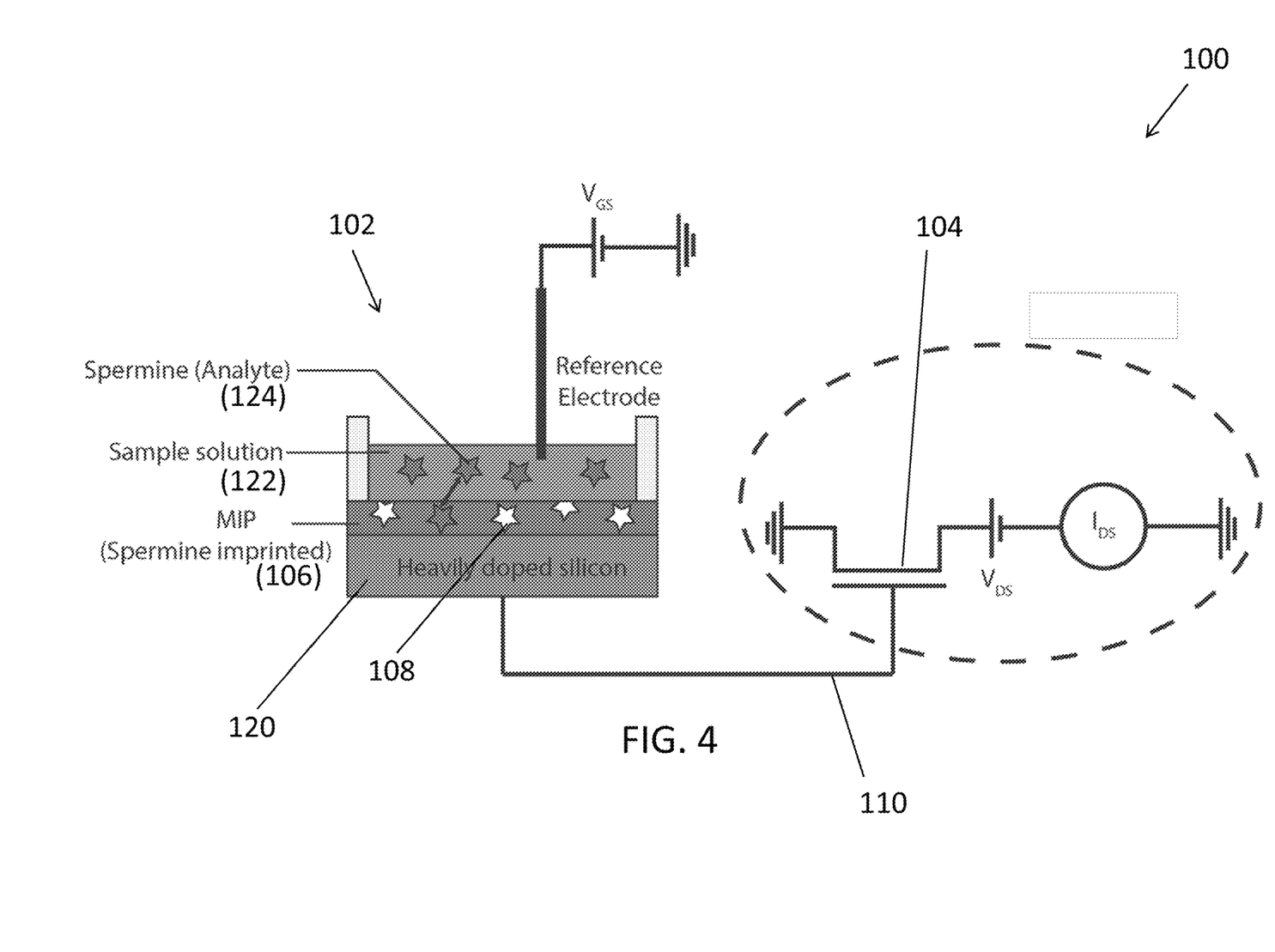
FIG. 4 is an illustration showing an example operation of detecting a polyamine or its derivatives with the apparatus of FIG. 1.

With reference to FIG. 4, there is illustrated an example embodiment of a method of determining a presence or an amount of a polyamine or its derivative in a sample, comprising the steps of: applying the sample on an electrochemical detector having a substance selection structure, wherein the substance selection structure is sensitive to the polyamine or its derivative; applying at least one voltage bias to the electrochemical detector; and detecting a change of electrical characteristics of the electrochemical detector so as to determine the presence or the amount of the polyamine or its derivative in the sample.

In this example, an analyte solution 122 which contains the target substance such as urinary spermine is applied on a surface of MIP layer 106 of the substance selection structure 102. As discussed earlier in this disclosure, when the MIP 106 accommodates one or more spermine molecules 124 in the analyte solution which is in contact with the MIP layer 106, which leads to a change of permittivity/dielectric constant of the MIP layer 106, and may also lead to a change in a differential capacitance of the substance selection structure 102, the electrical characteristic of the electronic device 104 is altered. As a result, the threshold voltage and/or source-drain current are altered. Such change in electrical characteristics of the FET device 104 corresponds to the concentration of the detected target substance in the analyte solution 122, and the change may be characterized by conventional electrical measurement unit for characterizing a transistor or other types of electronic devices.

For example, a high impedance (gigaohm) voltmeter, a nano-ammeter, a semiconductor parameter analyzer or an electrical source-meter unit (SMU) such as Keithley 2400 series may be used in the measurement steps. Example applied voltage bias may include a gate voltage of 3V and source-drain voltage of 3V. A small amount (such as 20-30 μL) of analyte solution is sufficient for the detection of the target substance.

In an example measurement setup, referring to FIG. 4, the analyte solution 122 is dropped on the extended gate sensor. A reference electrode is dipped into the sample solution 122. Using an SMU unit, a positive gate voltage ($V_{GS}$) is applied though the reference electrode and at the same time a positive drain-source voltage ($V_{DS}$) is applied to the FET device 104. The signal is read out as a function of the threshold voltage shift of the FET device 104 or the change in saturation drain current ($I_{DS}$) at a fixed gate voltage ($V_{GS}$) and source-drain voltage ($V_{DS}$).

Polyamines, particularly urinary spermine, may be used as a non-invasive biomarker for screening prostate cancer. Preferably, the detection of urinary spermine in a sample may be implemented by field effect transistor (FET) based sensors owing to their low cost and simple fabrication process. The sensors may be further implemented with a modular design which may enable the combinations to different types of biomarkers in urine for different diseases detection. In addition, these modular devices may be fabricated by printing in large and flexible substrates.

In one example embodiment of the present invention, the detection of polyamine is implemented with an electrochemical apparatus 100 based on selective bonding of polyamine or its derivatives in an aqueous sample. The sample may be a biological sample in particular a urine sample. The apparatus may be used to detect extremely low levels (ppb) of polyamine with appropriate receptors or sensing electrodes, thus providing a cost-effective, accurate and reliable means for polyamine detection in the sample.

Figure 5:
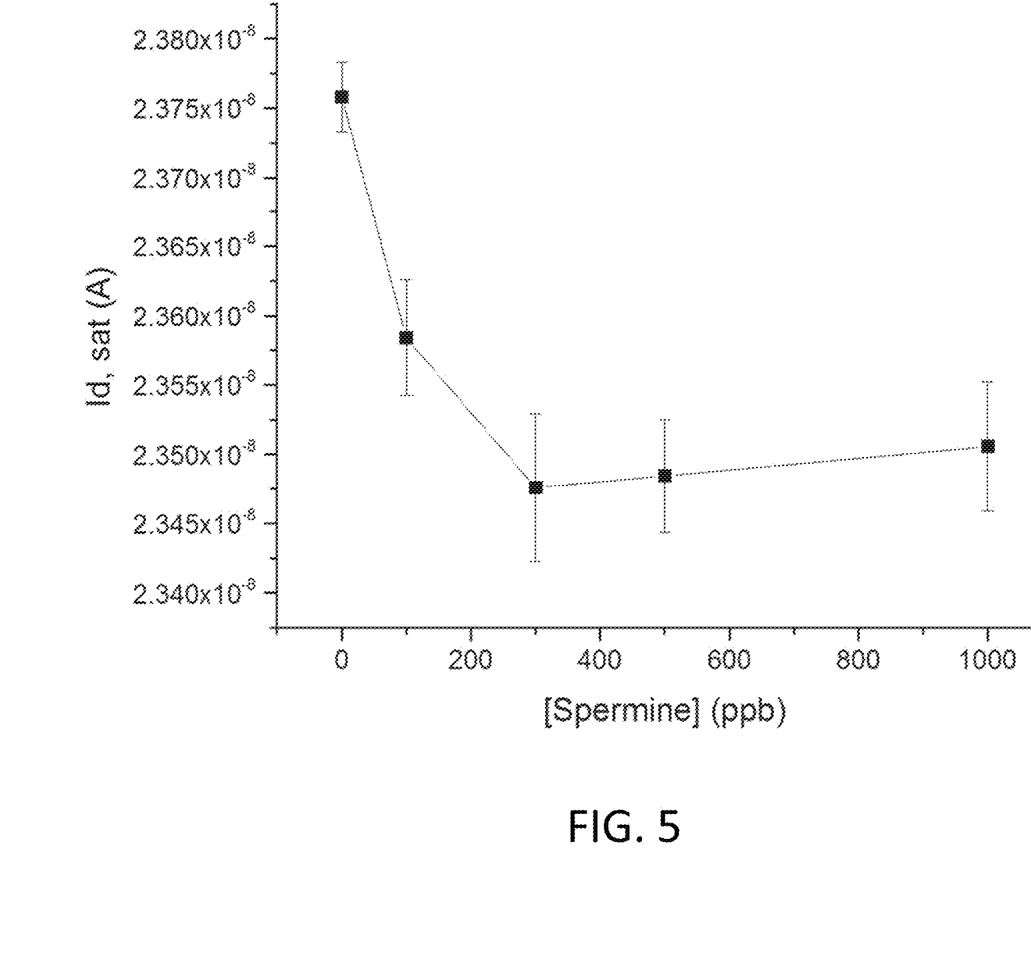
FIG. 5 is a plot showing calibrated values of the drain currents for various concentrations of spermine based on the example operation as shown in FIG. 4.

With reference to FIG. 5, there is shown a measurement result of the setup for the detection of 0, 100, 300, 500 and 1000 ppb of spermine in an artificial urine sample with drain current ranged from $2.345 \times 10^{-8}$ to $2.375 \times 10^{-8}$ A. Particularly, it is shown that the electrochemical apparatus 100 has a sharp detection response from 0 ppb to 300 ppb, indicating a high sensitivity of the electrochemical apparatus 100.

The inventors have, through their own research, trails and experiments, devised that low spermine concentration, such as <300 ppb, in urine may be a characteristic of prostate cancer. With reference to the above-mentioned experimental results, the electrochemical apparatus 100 may be applied for diagnosing prostate cancer in a subject such as a human by determining the concentration of urinary spermine in a sample associated with the subject.

These embodiments are advantageous in that the electrochemical apparatus may be implemented in portable electronic devices and hand-held sensors which may be used in domestic applications so as to provide a point-of-care service to the patients. The low-voltage operation of the electrochemical apparatus ensures chemical stability (no induced electrolysis) of analyte solutions.

Advantageously, the performance of the detection shows that the electrochemical detector has high selectivity and sensitivity for urinary spermine with the MIP electrode. The solid-state MIP layer may be easily tuned for selectively sensing different polyamine molecules (reversible & non-reversible), such as but not limited to spermidine, putrescine, N-acetylspermine, N1-acetylspermidine, N8-acetylspermidine, etc. or other types of molecule of interest by fabricating different MIP 106 with different molecule templates. In addition, solid-state molecule-selective electrode (the extended gate) 102 requires no internal filling solution.

The fabrication process is also simple and the electrochemical apparatus may be readily fabricated using different simple fabrication processes including low-cost fabrication methods such as printing and solution processing with low-cost materials. In addition, the substance selection structure and the electronic device structure may be separately fabricated on different substrates which may further simplify the fabrication process involved. The fabrication of the electrochemical apparatuses may be easily scaled up.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. An electrochemical apparatus, comprising:
   a substance selection structure including a spermine-specific molecular imprinted polymer layer specifically configured to chemically bind with spermine in a sample; and
   an electronic device in electrical connection with the spermine-specific molecular imprinted polymer layer;
   wherein when the sample is in contact with the spermine-specific molecular imprinted polymer layer, the chemical binding of spermine in the sample with the spermine-specific molecular imprinted polymer layer changes an electrical characteristic of the electronic device for indicating presence or an amount of spermine in the sample.

2. The electrochemical apparatus in accordance with claim 1, wherein the sample includes a biological sample.

3. The electrochemical apparatus in accordance with claim 2, wherein the biological sample includes a urine sample and the spermine is urinary spermine.

4. The electrochemical apparatus in accordance with claim 1, wherein the change of electrical characteristics of the electronic device is induced by a change in a differential capacitance of the substance selection structure.

5. The electrochemical apparatus in accordance with claim 4, wherein the change of electrical characteristics of the electronic device is induced by a change in permittivity and/or change in dielectric constant of the spermine-specific molecular imprinted polymer layer as a result of the spermine in the sample chemically binding with the spermine-specific molecular imprinted polymer layer.

6. The electrochemical apparatus in accordance with claim 1, wherein the electronic device includes a transistor.

7. The electrochemical apparatus in accordance with claim 6, wherein the substance selection structure is in electrical communication with a gate electrode of the transistor.

8. The electrochemical apparatus in accordance with claim 6, wherein the substance selection structure is arranged to operate as a gate electrode of the transistor.

9. The electrochemical apparatus in accordance with claim 6, wherein the electrical characteristic includes a threshold voltage of the transistor.

10. The electrochemical apparatus in accordance with claim 6, wherein the electrical characteristic includes a saturation drain current across the transistor under a predetermined gate bias and a predetermined source-drain bias.

11. The electrochemical apparatus in accordance with claim 10, wherein the gate bias is applied across the sample on applied on the substance selection structure, the substance selection structure and the transistor.

12. The electrochemical apparatus in accordance with claim 10, wherein the spermine-specific molecular imprinted polymer layer has a thickness of about 50 μm to 100 μm.

13. The electrochemical apparatus in accordance with claim 6, wherein the transistor comprises a thin-film transistor.

14. The electrochemical apparatus in accordance with claim 6, wherein the transistor comprises metal-oxide-semiconductor field-effect transistor.

15. The electrochemical apparatus in accordance with claim 1, wherein the electrochemical apparatus is a prostate cancer screening device.

16. The electrochemical apparatus in accordance with claim 15, wherein the prostate cancer screening device is a portable device.

17. The electrochemical apparatus in accordance with claim 15, wherein the prostate cancer screening device is a handheld device.

18. A prostate cancer screening device, comprising:
   a substance selection structure including a spermine-specific molecular imprinted polymer layer specifically configured to chemically bind with urinary spermine in a urine sample of a subject; and
   a transistor in electrical connection with the spermine-specific molecular imprinted polymer layer;
   wherein when the urine sample is in contact with the spermine-specific molecular imprinted polymer layer, the chemical binding of urinary spermine in the urine sample with the spermine-specific molecular imprinted polymer layer changes an electrical characteristic of the transistor for indicating presence or an amount of urinary spermine in the urine sample hence a possibility of the subject suffering from prostate cancer.

* * * * *